United States Patent [19]

Bruckenstein et al.

[11]  4,228,400

[45]  Oct. 14, 1980

[54] CONDUCTOMETRIC GAS ANALYSIS CELL

[75] Inventors: Stanley Bruckenstein, Amherst; Gregory A. Martinchek, Buffalo, both of N.Y.

[73] Assignee: Research Corporation, New York, N.Y.

[21] Appl. No.: 890,951

[22] Filed: Mar. 28, 1978

[51] Int. Cl.² ............................................. G01N 27/42
[52] U.S. Cl. ...................................... 324/450; 324/449
[58] Field of Search ........................... 324/30 B, 30 R; 204/195 R, 195 M, 195 P; 340/237 R; 73/23

[56] References Cited

U.S. PATENT DOCUMENTS

| | | | |
|---|---|---|---|
| 2,741,912 | 4/1956 | Schultze | 73/23 |
| 2,913,386 | 11/1959 | Clark | 204/195 P |
| 3,755,800 | 8/1973 | Purt et al. | 340/237 R |
| 3,864,659 | 2/1975 | Furuuchi et al. | 338/35 |
| 3,942,357 | 3/1976 | Jankins | 73/23 |
| 3,966,579 | 6/1976 | Chang | 324/30 R |
| 4,076,596 | 2/1978 | Connery | 204/195 P |
| 4,087,743 | 5/1978 | Bressan | 324/30 R |

Primary Examiner—Michael J. Tokar
Attorney, Agent, or Firm—Harold L. Stowell

[57] ABSTRACT

A conductometric gas analysis cell comprised of a porous Teflon membrane supporting interdigited electrodes separates a thin layer of deionized water from a gas phase to be analyzed. Volatile species in the gas phase pass through the membrane and increase the conductance of the water which results in increased current flow between the interdigited electrodes.

13 Claims, 9 Drawing Figures

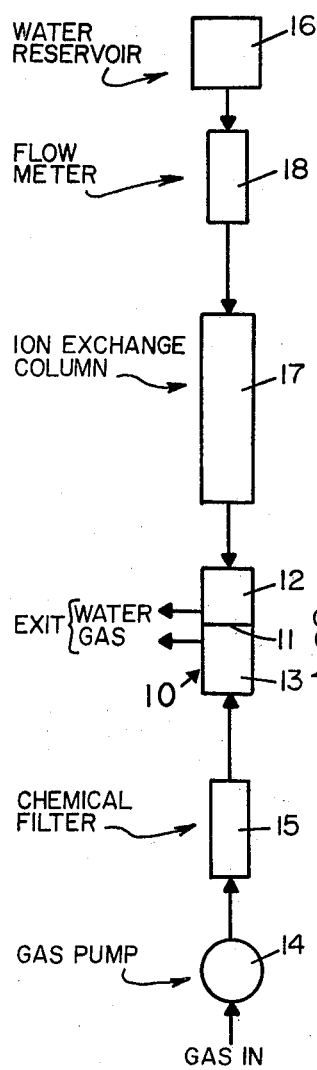
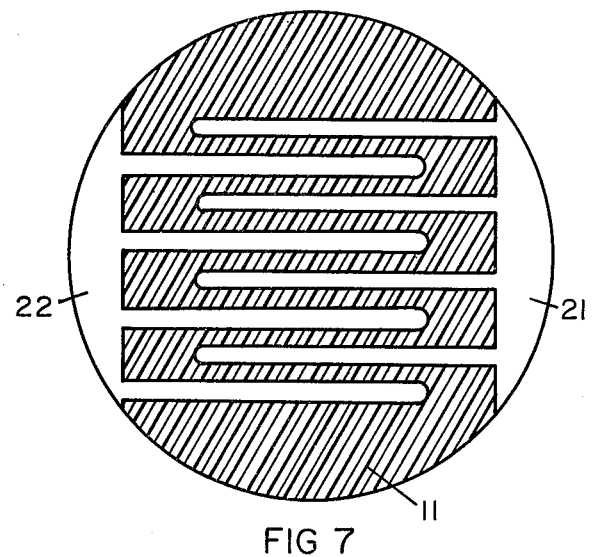
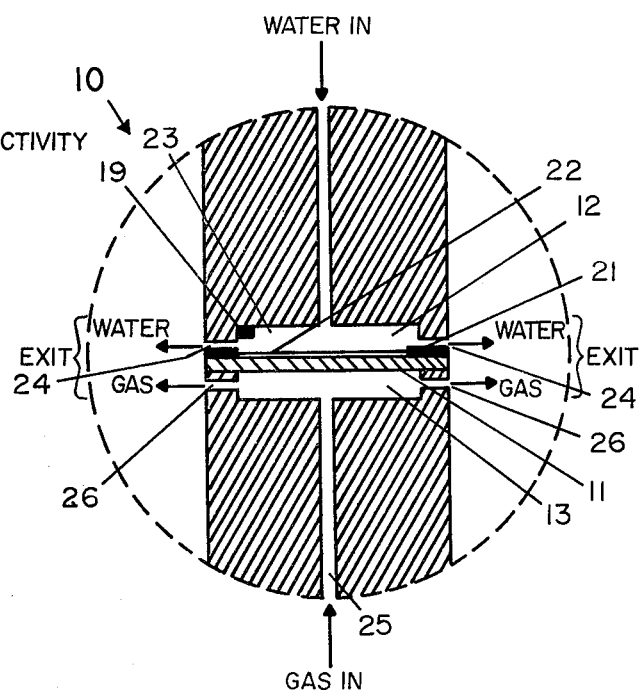

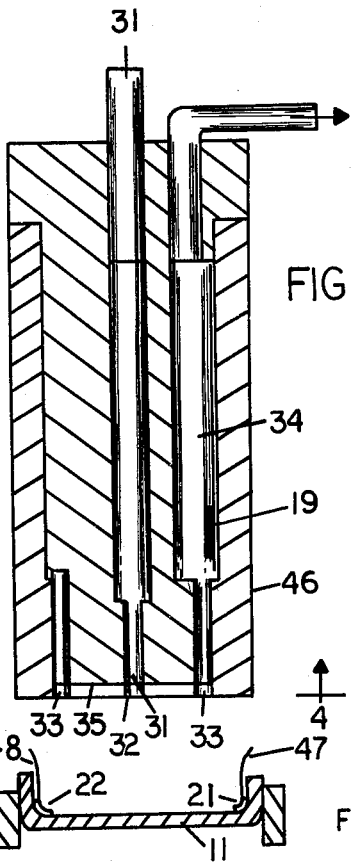
FIG 3
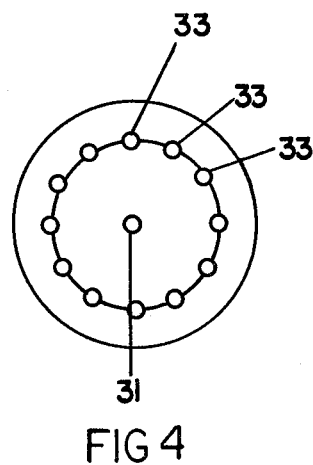
FIG 4
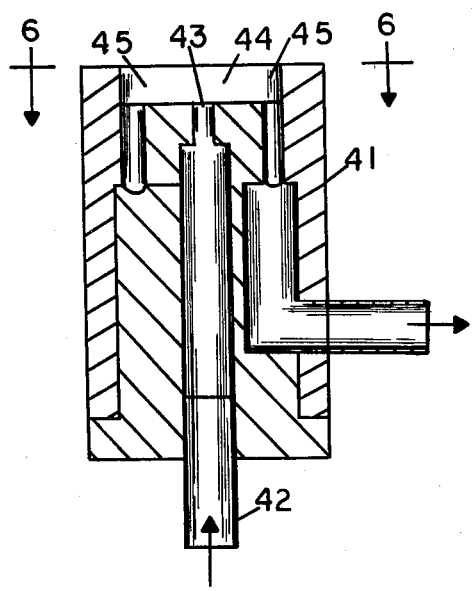
FIG 7a
FIG 5
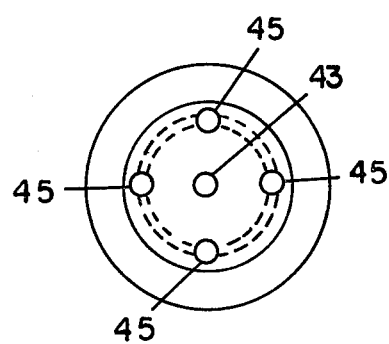
FIG 6

CONDUCTOMETRIC GAS ANALYSIS CELL

THE INVENTION

This invention relates to a means to determine the relative quantity of a specific gas in a sample as a function of the change in conductivity of a liquid in which the gas is dissolved.

BACKGROUND OF THE INVENTION

A great need exists for a relatively small device to determine the existence of an undesirable amount of specific gases in an atmospheric environment. For instance, the mining industry has a need to know when the levels of carbon dioxide or an explosive gas within a mine reach dangerous levels. Another area of concern is with respect to operators of closed vehicles such as aircraft and automobiles which are involved in an undetermined number of accidents resulting directly from the operators being overcome by carbon monoxide leaking from the engine exhaust systems into the operator compartments.

A number of devices are presently available which will identify gases in atmospheric environments but they are either expensive, bulky or relatively inaccurate. For instance, existing conductometric analyzers require bubbling of the gas stream being analyzed through a solution. This type of device requires a pump to force the gas sample through the solution and the devices are relatively heavy and not portable since they require power line connections or extremely heavy battery packs. Furthermore, they are not suitable for continuous monitoring under field conditions and are relatively expensive.

The known prior art conductometric gas analyzers mix the gas and water, remove gas bubbles from the water phase, and then pass the water containing the dissolved species over large conductometric electrodes. Gas and liquid flow rates are high and the apparatus required is heavy and bulky. Commercial conductometric analyzers presently on the market use flow rates as high as 1,000 milliliters of water per minute.

Another example of a gas detecting apparatus presently available is described in the patent issued to Schultze, U.S. Pat. No. 2,741,912 on "Apparatus for Detecting Gases or Vapors." This type of device is based on the principle that activated carbon increases in conductivity when exposed to harmful gases and vapors. Devices of this nature are subject to contamination build up and therefore do not provide an accurate indication of the instantaneous quality of the atmosphere being monitored.

G. Purt et al, U.S. Pat. No. 3,755,800 on "Automatic Fire Alarm Device" is exemplary of another approach to determining the presence of dangerous gases in an atmospheric environment. Devices such as Purt et al function on the principle that a catalytic reaction will occur when the dangerous gas contacts an anode in an electrolytic cell. The catalytic reaction causes an electrical current to be generated which may then be used to sound an alarm. Devices such as this are generally incapable of providing accurate measurements of the percentage of dangerous gas in the atmosphere and are only responsive to a limited number of elements.

OBJECTIVES OF THE INVENTION

In view of the obvious inability of the prior art systems to provide an economical, small gas analyzer to meet the needs of various industries and the population in general, it is a primary objective of the present invention to provide a conductometric gas analyzer which is small, accurate, and relatively inexpensive.

A further objective of the present invention is to provide a conductometric gas analyzer utilizing a porous or permeable membrane to separate a thin layer of deionized water from a gas phase to be analyzed.

A further objective of the present invention is to provide a relatively simple conductometric gas analyzer which may be powered by a relatively small battery source.

A still further objective of the present invention is to provide a portable gas analysis monitor which utilizes compressed gas or liquid having a high vapor pressure such as Freon to pressurize a water chamber and cause water to flow in a thin layer over conductometric electrodes.

It is a still further objective of the present invention to provide a conductometric gas analyzer which incorporates a porous Teflon membrane supporting interdigited conductometric electrodes and separating a thin layer of deionized water from a gas phase.

A further objective of the present invention is to provide a hydrophobic porous membrane adapted to support interdigited electrodes and a relatively thin film of water.

SUMMARY OF THE INVENTION

Presented hereby is a conductometric gas analyzer which includes a hydrophobic porous or gas permeable membrane which eliminates the need for mixing gas and liquid phases. The membrane supports two sets of interdigited electrodes and a thin film of a liquid such as deionized water on one side and the other side is subjected to the gas to be analyzed. The gas phase passes through the membrane and is immediately dissolved in the deionized water wherein it increases the water's conductivity. The increase in conductivity is then measured as a function of current flow between the interdigited electrodes.

DESCRIPTION OF THE DRAWINGS

FIG. 1 is a functional diagram of the conductometric gas analyzer of the present invention.

FIG. 2 is an exploded view of a preferred embodiment of the thin layer conductivity cell of the present invention.

FIG. 3 is a cross-section view of the water inlet for a preferred embodiment of the present invention.

FIG. 4 is a cell face end view of the water inlet embodiment of FIG. 3.

FIG. 5 is a cross-section view of the gas inlet of a preferred embodiment of the present invention.

FIG. 6 is a cell face end view of the gas inlet of FIG. 5.

FIG. 7 is the porous membrane of a preferred embodiment of the present invention as viewed from the electrode and water side.

FIG. 7a illustrates the porous membrane of FIG. 7 with a heat shrunk plastic band adapted to receive the ends of the cell forming members of FIGS. 3 and 5.

DESCRIPTION OF THE INVENTION

Figure 8:
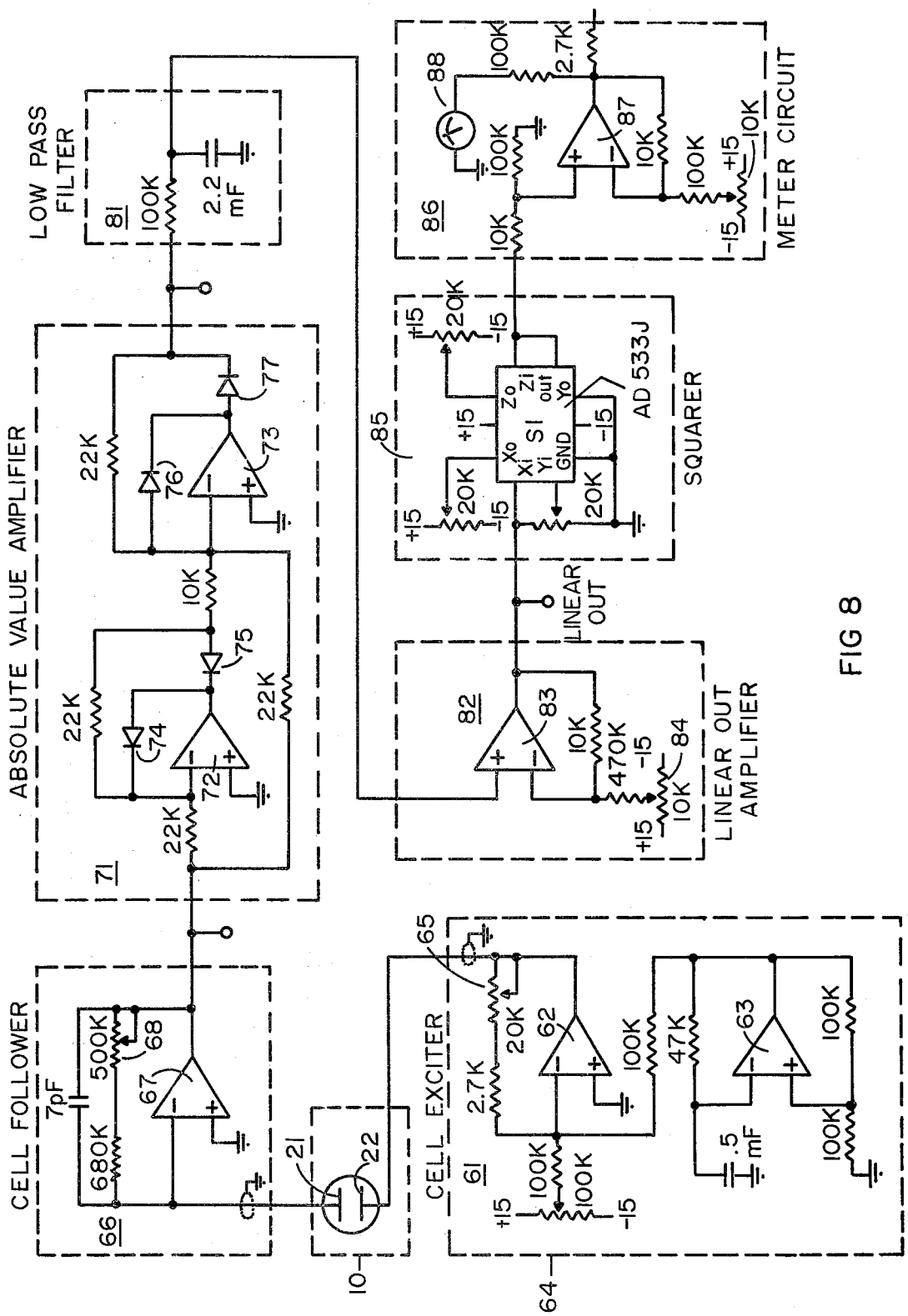
FIG. 8 is a schematic diagram of an electronic circuit of a preferred embodiment utilizing the conductometric gas analysis cell of the present invention to produce an indication.

FIG. 1 illustrates a preferred embodiment of the present invention in functional block form. The conductivity cell 10 includes a gas porous membrane 11 which separates a deionized water chamber 12 and a gas sample chamber 13. The gas sample chamber is supplied by a pump 14 which may be electrical or manual. It forces air or the gas sample through a chemical filter 15 into the gas analysis chamber 13.

The chemical filter 15 is provided to eliminate gases which are of no concern but which will cause a response in the conductivity cell 10.

It is to be particularly pointed out that in certain instances it is not necessary to employ the pump 14 to provide an effective cell. For example, where the cell is designed to detect the presence of carbon dioxide in the ambient, the partition coefficient of carbon dioxide between a volume of gas and a volume of water is approximately unity (at room temperature) and its acid dissociation constant is so small that free gas diffusion is capable of transporting carbon dioxide present in the gas phase to the membrane and into the water compartment where the electrodes measure the conductivity. Thus, a suitable carbon dioxide sensing device is provided by merely exposing the gas chamber face of membrane 11 directly to the atmosphere, or the atmosphere to the membrane through a thin sheet of felted carbon paper, which has been saturated with an appropriate reagent.

Free diffusion of carbon dioxide from the atmosphere will proceed through the felted carbon filter, then through the membrane 11 into the water compartment containing the electrodes.

The mutual interference problem of particular gaseous species which are of no concern during the analysis is solved by using suitable absorbants and chemical reactants supported on solids. A wide variety of absorbants and chemical reactants exist in the literature, and in those cases where new problems arise, it is possible to devise absorbants and reactants to remove the interferences. We have found that activated charcoal will remove some nitrogen dioxide and sulfur dioxide from a gas stream and that activated charcoal treated with sodium bisulfate will remove nitrogen dioxide, sulfur dioxide and ammonia from a gas but it will not react with carbon dioxide. Basic absorbants will remove acid gases, passing ammonia. Brucine sulfate in sulfuric acid when supported on fire-brick will remove nitrogen dioxide from a gas stream to be analyzed for sulfur dioxide. Likewise, sodium bicarbonate increases the capacity of activated charcoal for nitrogen dioxide and sulfur dioxide removal.

The water chamber 12 is supplied with water from the reservoir 16 which is deionized in the ion exchange column 17 so that the water will be non-conductive until gas is dissolved therein through the porous membrane 11.

In one embodiment of the present invention, the water reservoir 16 includes a pump such as a flexible wall which enables an operator to cause a small charge of water to be injected into the water chamber 12 prior to each sample analysis and the water previously in water chamber 12 returns to reservoir 16 or goes to a waste-water container. In the alternate embodiment of the present invention, the water reservoir is pressurized and a flow meter 18 controls the rate at which water is forced into the water chamber 12. The water chamber is relatively small in that only a thin film of water is required on the surface of the gas porous membrane 11. Typically, the volume of water required on the membrane for a sample analysis is 0.013 milliliters. In the continuous flow embodiment of the invention, 0.1 milliliter per minute has been found to provide adequate operation of the device.

The conductance of the liquid in the water chamber 12 is a function of temperature; therefore, an embodiment is anticipated wherein a thermistor 19 monitors the temperature of the liquid and provides a compensation signal to the electronic processing circuitry.

FIG. 2 is an exploded cutaway view of the conductivity cell 10 of FIG. 1. It uses similar reference designators for identical elements. The gas porous membrane 11 is stretched between the water chamber 12 and the gas sample chamber 13.

The gas porous membrane 11 contains two sets of electrodes, 21 and 22 which are interdigited, see FIG. 7. Water flows in the thin gap between electrodes 21 and 22 on the membrane 11 and the insulating walls 23 of the cell and exits through holes 24 drilled at the extreme radius of the cell body. On the gas side, gas enters through an axial hole 25 and exits through holes 26 drilled at the extreme radius of the gas sample chamber.

The gas porous membrane 11 of FIGS. 2 and 7 may be produced from a porous Teflon membrane. The electrodes 21 and 22 are made of gold in a preferred embodiment and are of an interlocking finger design where alternate electrodes are electrically connected together to create two electrodes having relatively large interacting surface areas for the conductance measurement. Other noble metals may be used such as platinum, palladium and rhodium, and even stainless steel.

The electrodes may be prepared by painting a gold resinate on the porous Teflon membrane and heat curing it to leave an adherent gold layer having the illustrated pattern. Gold wires may be pressed against the contact pad areas to make electrical contact buses for the electrodes which are illustrated as the thick end portions of electrodes 21 and 22 from which the interdigited electrodes extend in FIG. 7. While in the illustrated embodiment of the invention interdigited electrodes are illustrated, other electrode arrangements would provide satisfactory results. For example, one electrode may be placed on the liquid side of the gas porous membrane and the other either in the middle of the liquid chamber or on a wall forming the liquid chamber. It will also be recognized by those skilled in the art that neither electrode need be on the gas porous membrane as long as both are in electrical contact with the liquid in the liqud chamber 12.

The conductivity cell may be assembled utilizing shrink tubing or various adhesives and compression seals.

In an alternate embodiment, the water side of the cell is formed from a plexiglass device similar to that illustrated in FIG. 3 wherein a central water tube 31 injects water into the thin layer depression 32 which fits over the membrane forming a space approximately 0.004 inches in depth and approximately 0.5 inches in diameter. The water flows from the central opening 31 across the membrane and exits through a plurality of bores 33 which form a circle about the periphery of the water chamber. In this embodiment the thermistor 19 will be located in the exhaust water chamber 34.

FIG. 4 is a diaphragm or cell face end view of the water inlet apparatus of FIG. 3. Note that the plurality of exit orifices 33 are equally spaced about the water inlet 31 to form an outer circle thereabout. The water inlet 31 and each of the outlets 33 are of identical diameters which, in the illustrated embodiment are 0.064 inches.

FIG. 5 illustrates a gas inlet assembly adapted to function in combination with the water inlet assembly of FIGS. 3 and 4. The gas inlet assembly includes a Teflon housing 41 which supports a gas inlet tube 42 fabricated from, for example, Pyrex tubing. The gas inlet 42 has a small opening 43 through which gas enters the gas sample chamber 44 which is slightly larger than the water chamber 35 due to its increased depth. When the gas exits orifice 43 it flows over the gas side of the porous membrane and out exit orifices 45.

FIG. 6 is an end view of the gas inlet illustrated in FIG. 5 looking from the gas porous membrane. The gas inlet 43 is surrounded by four gas outlets 45 which are of equal diameter. In the illustrated embodiment, the orifices are 3/32 of an inch in diameter.

To complete the assembly, a membrane 11 having electrodes 21 and 22 is stretched over the end of the water side of the cell 46 in FIG. 3. Gold wires 47 and 48 are pressed against the contact pads of electrodes 21 and 22. The water side 46 and the gas side 41 of the cell are held against the membrane 11 by heat shrunk tubing 34'.

Conductometric measurements are performed using electronic circuitry similar to that illustrated in FIG. 8. In this circuit, a square wave voltage is applied across electrodes 22 and 21 located in the conductivity cell 10. One set of electrodes 22 is driven by a cell exciter 61 which includes a pair of amplifiers 62 and 63 that are interconnected with appropriate resistive and capacitive elements to generate a pulsating square wave. The amplitude of the square wave applied to electrode 22 is controlled by potentiometer 65 in a feedback loop for amplifier 62. Potentiometer 64 controls the symmetry of the square wave pulses produced by the cell exciter. The desired square wave form is one having equal positive and negative magnitudes, each of equal duration. A frequency of 200 Hz was used.

Electrodes 21 of the conductivity cell 10 are coupled to cell follower 66 which includes an amplifier 67 that provides a square wave output having an amplitude which is a function of the conductivity of cell 10. The square wave output amplifier 67 is adjusted by calibration potentiometer 68 to compensate for various system irregularities and, in one proposed embodiment, the feedback circuit for amplifier 62 or amplifier 67 will include thermistor 19 to compensate for temperature variations in the water.

The square wave pulse output of amplifier 67 is applied to the absolute value amplifier 71 which includes a pair of cascaded amplifiers 72 and 73. These amplifiers function in association with diodes 74 and 75 and 76 and 77 respectively which function as a full wave bridge rectifier in combination with the amplifiers. Thus the absolute value amplifier 71 rectifies the square wave output of cell follower 66 and provides DC output.

The rectified output of absolute value amplifier 71 is applied to low pass filter 81 which functions to eliminate any ripple resulting from the rectification operation.

The filtered DC output from low pass filter 81 is applied to the linear output amplifier 82 which includes an amplifier 83 having a feedback circuit including a 0 adjustment potentiometer 84. If desired, the thermistor 19 illustrated in FIG. 2 and FIG. 7a may be incorporated in the feedback circuit of amplifier 62 or amplifier 67. The output of amplifier 83 is applied to squarer 85 which in an integrated circuit which squares the analog output of linear output amplifier 82. The output of squarer 85 is applied to meter circuit 86 which includes an amplifier 87 and a meter 88.

In a preferred embodiment, amplifiers 62, 63, 72, 73, 83, and 87 are integrated circuit types LM324 and amplifier 67 is an LH0022. The squarer is integrated circuit AD533J.

In FIG. 8, a square wave voltage across electrodes 21 and 22 is rectified to provide an indication but a sine wave alternating voltage measurement may be used as an alternate embodiment.

The conductance between electrodes depends not only upon the concentration of the species which dissolves to form ions, but also upon the rate of flow of the water in the cell. Thus, the water flow rate must be held constant by the flow meter apparatus 18 of FIG. 1. Depending upon the gas being analyzed, a certain minimum gas flow rate must be exceeded in order to obtain conductance readings independent of gas flow rate. The higher the solubility of the gaseous species in water, the larger the required gas flow rate. For sparingly soluble carbon dioxide, a very low gas transport rate, for example, that produced by free diffusion and natural convection is sufficient. Gas flow rates on the order of several hundred milliliters per minute are required for more soluble gases such as sulfur dioxide and ammonia. Such gas flow rates are readily produced using commercially available gas pumps for gas pump 14 of FIG. 1.

The cell may be operated in a stationary water flow situation by first flushing the thin layer cell with water, then stopping the water flow and then exposing the cell to the gas stream. This method of operation has the advantage that water flow rate need not be controlled, and uses very small quantities of water, making possible a miniature hand-held detector. In the preferred embodiment, the water flushed from the thin layer cell is returned to water reservoir 16 by appropriate one-way valves for subsequent reuse.

An embodiment utilizing water and gas inlet flow means such as illustrated in FIGS. 3 through 6 may be used to produce an embodiment having physical dimensions less than 2 inches long and 1½ inches in diameter, including the gas inlet system, membrane, water inlet system and mixed bed ion exchange resin.

Theory predicts the conductance of a solution of a volatile weak electrolyte in equilibrium with a gas phase will be proportional to the square root of the gas phase concentration of the molecular form of the electrolyte. Thus, a linear calibration curve should be obtained when conductance squared is plotted versus gas phase concentration of the species of interest. The data in Table I demonstrates the validity of this relationship for a range of $CO_2$ concentrations run through a thin layer cell in single reading mode.

TABLE I

| $CO_2$ Calibration Using a Cell in Single Pulse Mode | | | |
|---|---|---|---|
| $CO_2$ Conc. (ppm $CO_2$) | Conductance ($\mu$mho) | Conductance Squared ($\mu$mho)$^2$ | Least Squares Fit ($\mu$mho)$^2$ |
| 0 | 0.12 | 0.02 | −0.01 |
| 500 | 0.86 | 0.74 | 0.61 |
| 1000 | 1.17 | 1.38 | 1.22 |
| 2000 | 1.54 | 2.36 | 2.46 |
| 2000 | 1.56 | 2.43 | 2.46 |
| 5000 | 2.42 | 5.88 | 6.17 |

TABLE I-continued

CO₂ Calibration Using a Cell in Single Pulse Mode

| $CO_2$ Conc. (ppm $CO_2$) | Conductance ($\mu$mho) | Conductance Squared ($\mu$mho)$^2$ | Least Squares Fit ($\mu$mho)$^2$ |
|---|---|---|---|
| 7500 | 2.99 | 8.94 | 9.26 |
| 7500 | 3.08 | 9.48 | 9.26 |
| 10000 | 3.56 | 12.60 | 12.35 |

Gas Flowrate 0.5Lmin$^{-1}$, Data Recorded 60 seconds after the H$_2$O Pulse. Instrument Sensitivity 1$\mu$mho/volt. Conductance Squared column generated from the recorded conductances. Least Squares Fit column from least squares fit of the Conductance Squared column.

As hereinbefore set forth, a continuous readout device can also be constructed using the same thin layer cell. Instead of a pulse of water intermittently replacing the entire water sample, a very low flow of water continuously replaces the thin layer water sample.

Response times to step changes in gas concentrations are shorter at higher water flowrates. At a water flowrate of 100 $\mu$Lmin$^{-1}$ a response time of 20 seconds to 95% of the final reading is typical. At a water flowrate of 500 $\mu$Lmin$^{-1}$ the response time approaches 2 seconds.

Sample gas flow is required to supply the aqueous phase with the substance of interest. Unlike the single reading equilibrium case, there must be a continuous flux from the gas phase to the thin layer. Gas sample flowrate must exceed a minimum for conductance to be independent of gas flowrate. The minimum gas flowrate required is dependent on the water flowrate. With a water flowrate of 100 $\mu$Lmin$^{-1}$, the conductance due to gas phase $CO_2$ is constant with gas flowrates from 10 mLmin$^{-1}$. For $SO_2$ and the same water flowrate, conductance is only independent of gas flowrate with flows in excess of 300 mLmin$^{-1}$.

Experimentally, it has been found that the square of conductance is proportional to gas phase concentration of $CO_2$ and $SO_2$ only at low ($<$150 $\mu$Lmin$^{-1}$) water flowrates. At higher water flowrates, plots of conductance squared versus gas concentration become concave upward. Tables II and III demonstrate the linearity of the calibration for various $CO_2$ and $SO_2$ concentrations run through a continuous readout cell at low water flowrates.

TABLE II

CO₂ Calibration Using a Cell in Continuous Flow Mode

| $CO_2$ Conc. (ppm $CO_2$) | Conductance ($\mu$mho) | Conductance Squared ($\mu$mho)$^2$ | Least Squares Fit ($\mu$mho)$^2$ |
|---|---|---|---|
| 0 | 0.41 | 0.18 | 0.25 |
| 200 | 0.66 | 0.44 | 0.44 |
| 500 | 0.83 | 0.68 | 0.74 |
| 800 | 1.04 | 1.07 | 1.03 |
| 1000 | 1.15 | 1.31 | 1.23 |
| 1500 | 1.38 | 1.89 | 1.72 |
| 2000 | 1.50 | 2.25 | 2.22 |
| 2500 | 1.63 | 2.66 | 2.71 |
| 3500 | 1.93 | 3.72 | 3.70 |
| 5000 | 2.23 | 4.97 | 5.18 |
| 7500 | 2.77 | 7.67 | 7.65 |
| 10000 | 3.19 | 10.19 | 10.12 |
| 50000 | 7.17 | 53.8 | 49.6 |

Gas Flowrate 0.5Lmin$^{-1}$, Water Flowrate 140$\mu$Lmin$^{-1}$. Instrument Sensitivity 1$\mu$mho/volt. Conductance column generated from measured conductance squared instrument output. Least Squares Fit column from the least squares fit of the data in the Conductance Squared column.

TABLE III

SO₂ Calibration Using a Cell in Continuous Flow Mode

| $SO_2$ Conc. (ppm $SO_2$) | Conductance (mmho $\times$ 10) | Conductance Squared (mmho$^2$ $\times$ 100) | Least Squares Fit (mmho$^2$ $\times$ 100) |
|---|---|---|---|
| 0 | 0.03 | 0.00 | .02 |
| 23 | 0.56 | 0.31 | .34 |
| 32 | 0.74 | 0.55 | .49 |
| 65 | 1.06 | 1.12 | 1.0! |
| 106 | 1.32 | 1.74 | 1.67 |
| 166 | 1.65 | 2.72 | 2.63 |
| 220 | 1.87 | 3.50 | 3.50 |
| 345 | 2.26 | 5.11 | 5.50 |
| 412 | 2.53 | 6.40 | 6.58 |
| 528 | 2.91 | 8.47 | 8.44 |
| 665 | 3.30 | 10.89 | 10.63 |

Gas Flowrate 0.75Lmin$^{-1}$, Water Flowrate 91$\mu$Lmin$^{-1}$. Instrument Sensitivity 100$\mu$mho/volt. Conductance Squared column generated from the recorded conductance data. Least Squares Fit column from the least squares fit of the Conductance Squared column.

Gas monitors may be produced for hospitals, factories, mines, sewers and numerous other industrial applications based on the invention disclosed herein. Stack monitoring or following gas plumes in the atmosphere are further applications of the invention. This method of gas analysis may also be extended by adding various chemical reagents to the distilled water before it enters the cell and permit carrying out chemical reactions which lead to a change in conductance of the cell. The cell may also be used as a gas chromatographic detector. Therefore, preferred embodiments of this invention have been illustrated and described, variations and modifications may be apparent to those skilled in the art. Hence, we do not wish to be limited thereto and ask that the scope and breadth of this invention be determined from the claims which follow rather than the above description.

What we claim is:

1. A conductometric gas analysis apparatus, comprising: a conductivity cell; and said conductiviy cell comprises a gas permeable membrane having a liquid side and a gas side; a first electrode on said liquid side; a second electrode on said liquid side and spaced from the first electrode; a liquid chamber means for applying and renewing a thin film of liquid over said gas permeable membrane liquid side and said first and second electrodes, a gas chamber means associated with the gas side of the gas permeable membrane, liquid inlet and outlet means for said liquid chamber means, gas inlet means for said gas chamber means, and means for continuously supplying a liquid to the liquid inlet and a gas to be analyzed to the gas inlet.

2. A conductometric gas analysis apparatus, comprising: a conductivity cell; and said conductivity cell comprises a gas porous membrane having a liquid side and a gas side; a first electrode supported on said gas porous membrane liquid side; a second electrode supported on said gas porous membrane liquid side and spaced from the first electrode; a water chamber means for applying a thin film of water over said gas porous membrane liquid side and said first and second electrodes; and a gas chamber means for applying a gas to be analyzed to said gas porous membrane gas side, wherein said first and said second electrodes incorporate a plurality of interdigited elements.

3. A conductometric gas analysis apparatus as defined in claim 2, comprising: a water reservoir; means for deionizing water; means for transporting water from said water reservoir to said means for deionizing water;

and means for transporting water from said water deionizing means to said water chamber.

4. A conductometric gas analysis apparatus as defined in claim 3, comprising: a gas pump; and means to couple gas from said pump to said gas chamber.

5. A conductometric gas analysis apparatus as defined in claim 4 wherein said means to couple gas from said gas pump to said gas chamber comprises a filter means to eliminate predetermined gas constituents from said gas being transported from said gas pump to said gas chamber.

6. A conductometric gas analysis apparatus as defined in claim 5 wherein said filter means includes an absorbent.

7. A conductometric gas analysis apparatus as defined in claim 5 wherein said filter means includes a reactant.

8. A conductometric gas analysis apparatus as defined in claim 5, comprising: electric circuit means to apply an electric current between said first and said second electrodes; and means responsive to current flow between said first and said second electrodes for providing an indication representating the magnitude of said current flow.

9. A conductometric gas analysis apparatus as defined in claim 8, comprising: a thermistor responsive to the temperature within said water chamber; and means responsive to said thermistor for altering said indication.

10. A conductometric gas analysis apparatus as defined in claim 5 wherein said gas permeable member is a hydrophobic porous membrane.

11. A conductometric gas analysis apparatus as defined in claim 5 wherein said gas permeable member is a porous Teflon membrane.

12. A conductometric gas analysis apparatus as defined in claim 5 wherein said first and second electrodes are gold.

13. A conductometric gas analysis apparatus, comprising: a conductivity cell; and said conductivity cell comprises a gas permeable membrane having a liquid side and a gas side; a first electrode on said liquid side; a second electrode on said liquid side and spaced from the first electrode; a liquid chamber means for applying a thin film of liquid over said gas permeable membrane liquid side and said first and second electrodes, and a gas absorbent for said apparatus, said gas absorbent selected from the group consisting of activated charcoal treated with sodium bisulfate, activated charcoal treated with sodium bicarbonate, firebrick treated with brucine sulfate in sulfuric acid and firebrick treated with basic absorbants.

* * * * *